United States Patent [19]

Kanno et al.

[11] Patent Number: 4,869,256

[45] Date of Patent: Sep. 26, 1989

[54] ENDOSCOPE APPARATUS

[75] Inventors: Masahide Kanno; Hisao Yabe, both of Hachioji; Jun Yoshinaga, Hino; Takeshi Yokoi; Kazuhiko Oozeki, both of Hachioji, all of Japan

[73] Assignee: Olympus Optical Co., Ltd., Tokyo, Japan

[21] Appl. No.: 184,560

[22] Filed: Apr. 21, 1988

[30] Foreign Application Priority Data

Apr. 22, 1987 [JP] Japan .................................. 62-100907
Apr. 22, 1987 [JP] Japan .................................. 62-100906
Dec. 24, 1987 [JP] Japan .................................. 62-325237

[51] Int. Cl.⁴ .......................... A61B 8/00; A61B 8/12
[52] U.S. Cl. ........................ 128/660.04; 128/662.06; 128/6; 358/112
[58] Field of Search ............... 128/4, 6, 660.04, 660.7, 128/661.01, 662.06, 665; 73/625-626

[56] References Cited

U.S. PATENT DOCUMENTS 4,135,140  1/1979  Buchner ........................... 73/626 X
4,463,763  8/1984  Koyano et al. .................. 128/660.04
4,615,330  10/1986 Nagasaki et al. ........... 128/662.06 X
4,651,744  3/1987  Bristow et al. .................. 128/665 X

FOREIGN PATENT DOCUMENTS 58-133232  8/1983  Japan ....................................... 128/6
60-77731   5/1985  Japan ....................................... 128/6

Primary Examiner—Francis Jaworski
Attorney, Agent, or Firm—Armstrong, Nikaido, Marmelstein, Kubovcik & Murray

[57] ABSTRACT

An endoscope comprises an elongated inserting section having an illumination window and an observation window at a distal end portion thereof, an imaging device for forming an optical image of an object upon receiving light reflected from the object radiated through the observation window, and an ultrasonic probe disposed at the distal end portion of the inserting section and adapted to obtain an ultrasonic image of the object. A signal processing apparatus to which the endoscope is connected comprises: an optical-image signal processing device adapted to effect signal processing for the imaging device and to generate a video signal of the optical image and having an optical image memory device for storing the optical image, an ultrasonic-image signal processing device adapted to effect signal processing for the ultrasonic probe and to generate a video signal of the ultrasonic image and having an ultrasonic image memory device for storing the ultrasonic image, and a memory device control device which is adapted to control writing and reading by the optical image memory device and the ultrasonic image memory device, and which, when a moving ultrasonic image is viewed, makes it possible to display a still optical image, and, when a moving optical image is viewed, makes it possible to display a still ultrasonic image.

27 Claims, 14 Drawing Sheets

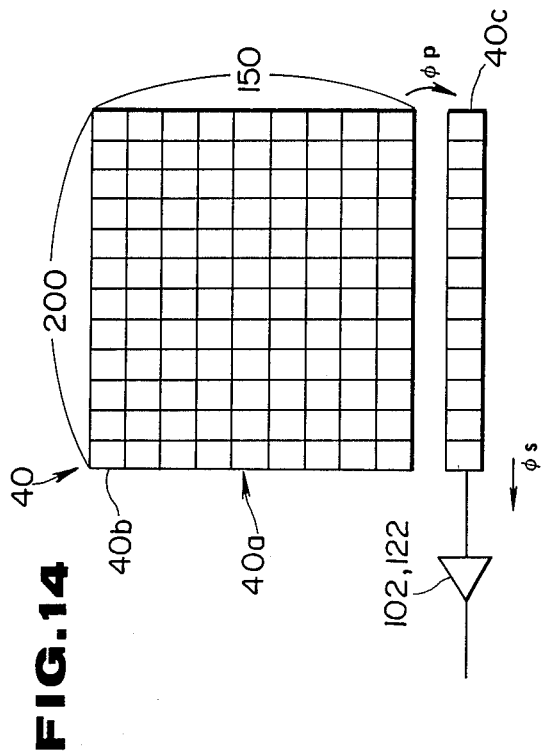
FIG.14
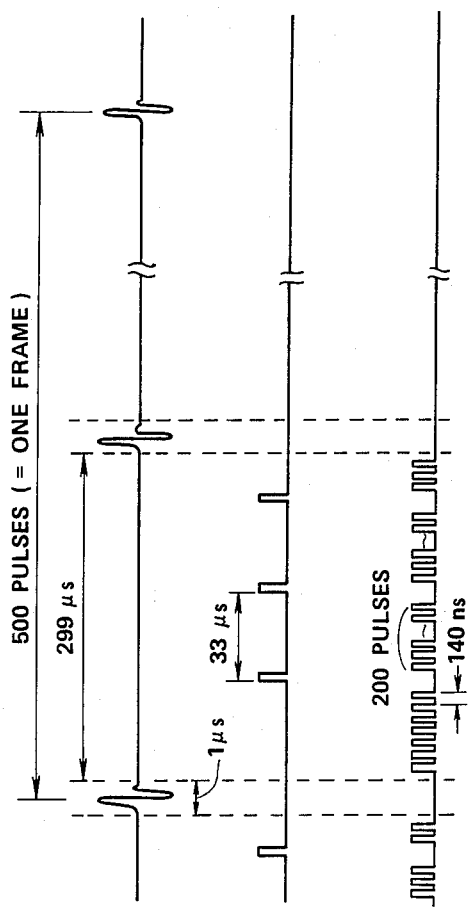
FIG.15 (A) ULTRASONIC PROBE DRIVE PULSE
FIG.15 (B) VERTICAL REGISTER CLOCK PULSE $\phi p$
FIG.15 (C) HORIZONTAL REGISTER CLOCK PULSE $\phi s$

FIG.16 (A) ULTRASONIC PROBE DRIVE PULSE
FIG.16 (B) TRANSMISSION SOUND PRESSURE FROM ULTRASONIC PROBE
FIG.16 (C) REFLECTED SOUND PRESSURE FROM LIVING ORGAN

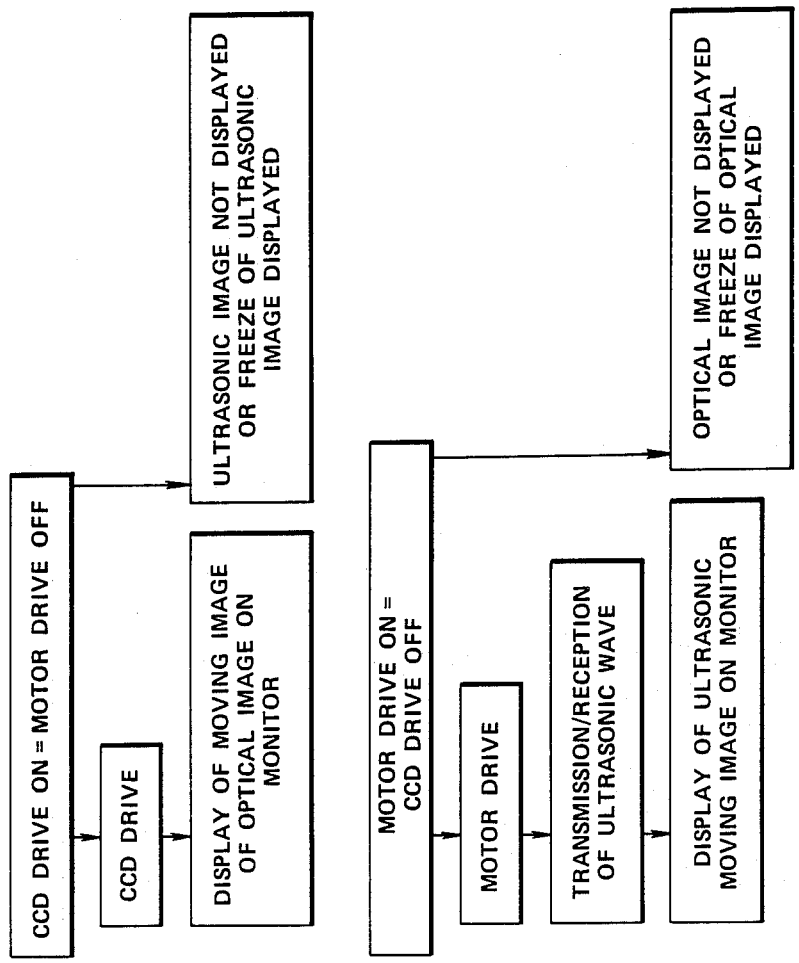

ENDOSCOPE APPARATUS

BACKGROUND OF THE INVENTION

1. Field of the Invention:

The present invention relates to an endoscope apparatus which is capable of obtaining an optical image and an ultrasonic image.

2. Related Art Statement:

In recent years, various electronic endoscopes have been proposed in which solid-state imaging devices such as charge-coupled devices (CCDs) are used as imaging means.

In addition, rapid development has been made in ultrasonic diagnosing apparatuses for diagnosing somatic tissues and organs. Recently, ultrasonic endoscopes have also been used in which probes are inserted into somatic cavities so as to allow the interior of somatic cavities to be observed endoscopically. In this ultrasonic endoscope, a vibrator is inserted into the body, and hence the tissue such as skin and the fat which attenuates ultrasonic waves is not interposed between the vibrator and an affected part to be diagnosed. Therefore, there are advantages in that the transmission of ultrasonic waves is excellent, and that it is possible to obtain images having a high degree of definition.

Furthermore, as disclosed in, for instance, Japanese Patent Laid-Open No. 133232/1983, an ultrasonic endoscope has been proposed which is arranged such that a means for obtaining an optical image such as a solid-state imaging device, and a means for obtaining an ultrasonic image are provided in a distal end portion of an inserting section, and relative positional relationships between the optical image and the ultrasonic image are clarified so as to allow the optical image and the ultrasonic image to correspond to each other.

In an endoscope apparatus which is provided with a solid-state imaging device as a means for obtaining an optical image and a vibrator as a means for obtaining an ultrasonic image, if an attempt is made to observe the optical image and the ultrasonic image simultaneously, a signal for imaging and a signal for obtaining the ultrasonic image are simultaneously transmitted and received through an elongated endoscope. This results in mutual interference of the signals, and a great amount of noise appears in the image, with the result that the image becomes difficult to observe. In particular, as for a drive pulse of the ultrasonic vibrator, a pulse value is extremely high at, for instance, 250V, so that there is a risk of pulse-like noise becoming mixed in an imaging signal line of the solid-state imaging device.

For that reason, while one image is being observed, it is possible to, for instance, completely stop the drive signal for the other image so as to prevent the mixing in of noise. In this case, however, the other image cannot be obtained at all, so that a hindrance is caused to observation. In particular, when the ultrasonic image is being observed, it is extremely important to ascertain by an optical image using the solid-state imaging device which part of the body the ultrasonic image being displayed pertains.

In addition, Japanese Patent Laid-Open No. 77731/1985 discloses a technique in which the ultrasonic oscillation is suspended during a period of reading by the solid-state imaging device. According to this related technique, the ultrasonic oscillation is suspended, for instance, during a period of 4 ms in one cycle of 33 ms. However, this period of suspension is long when compared with an ultrasonic pulse which is transmitted at a pulse width of 1 $\mu$s in a cycle of 300 $\mu$s, so that there is a problem in that an amount of information obtained from the ultrasonic image becomes small.

Furthermore, when a system is used in which an ultrasonic probe is made to mechanically scan to obtain an ultrasonic image, the following problem is encountered. If a motor, i.e., a driving means for causing the ultrasonic probe to mechanically scan, is driven while a drive pulse is being supplied from a solid-state imaging device driving means to a solid-state imaging device, the brush noise generated from the motor and the induction noise generated from various mechanical vibrations are induced to a signal cable for driving the solid-state imaging device. Hence, when an optical image is displayed on a monitor, the noise appears, with the result that the quality of the optical image is impaired, making it impossible to carry out proper diagnosis of the image.

On the contrary, if a drive pulse is sent to the solid-state imaging device while the motor, i.e., a driving means for causing the ultrasonic probe to mechanically scan, is being driven and a high-frequency pulse is being sent to the ultrasonic probe to effect ultrasonic scanning, the following problem is encountered. When the ultrasonic image is displayed on the monitor, noise appears on the monitor due to fluctuations in voltage caused at the time of changing over of this drive pulse, thereby causing a hindrance to proper diagnosis of the ultrasonic image.

In the above-described Japanese Patent Laid-Open No. 77731/1985, a proposal is made not to send the high-frequency pulse to the ultrasonic probe while the drive pulse is being supplied to the solid-state imaging device and reading of the signal is being carried out. However, since the motor for rotatively driving the ultrasonic probe is constantly operating, noise generated therefrom is not removed. A known apparatus is arranged such that an optical image observing apparatus and an ultrasonic image observing apparatus are operated by being changed over by means of two changeover switches so as to obviate the mutual interference caused by such noise. However, since the two changeover switches are not interlinked with each other, the operation is complicated, and has been particularly troublesome when the optical image and the ultrasonic image are changed over frequently.

OBJECT AND SUMMARY OF THE INVENTION

Accordingly, an object of the present invention is to provide an endoscope apparatus which is capable of obtaining both an optical image and an ultrasonic image which have a small amount of noise and of observing one image when the other image is being observed.

Another object of the present invention is to provide an endoscope apparatus which makes it possible to simultaneously observe an optical image and an ultrasonic image and which produces less adverse effect on an amount of information and suffers less noise.

To these ends, an endoscope apparatus in accordance with the present invention has an endoscope and a signal processing apparatus for the endoscope. The endoscope comprises an elongated inserting section having an illumination window and an observation window at a distal end portion thereof. An imaging device forms an optical image of an object upon receiving light reflected from the object radiated through the observation window. An ultrasonic probe is disposed at the distal end portion of the inserting section and adapted to obtain an ultrasonic image of the object. The signal processing apparatus for use in the endoscope comprises: an optical-image signal processing device adapted to effect signal processing for the imaging device and to generate a video signal of the optical image and having an optical image memory device for storing the optical image. An ultrasonic-image signal processing device effects signal processing for the ultrasonic probe and generates a video signal of the ultrasonic image and has an ultrasonic image memory device for storing the ultrasonic image. A memory control device which is adapted to control writing and reading by the optical image memory device and the ultrasonic image memory device, and which, when a moving ultrasonic image is viewed, makes it possible to display a still optical image, and, when a moving optical image is viewed, makes it possible to display a still ultrasonic image.

The other objects, features and advantages of the present invention will become more apparent from the following description of the invention when read in conjunction with the accompanying drawings.

BRIEF DESCRIPTION OF THE DRAWINGS

FIGS. 1 to 7 relate to a first embodiment of the present invention, in which

FIG. 1 is a block diagram illustrating a configuration of an endoscope apparatus;

FIG. 2(A) is a diagram schematically illustrating an external appearance of the endoscope apparatus;

FIG. 2(B) is a diagram schematically illustrating a monitor which is displaying an optical image;

FIG. 3 is a cross-sectional view of a distal end portion of a video ultrasonic scope;

FIG. 4 is a block diagram illustrating an example of a front-stage image processing circuit of a frame sequential system.

FIG. 5 is a block diagram illustrating an example of the front-stage image processing circuit of a simultaneous system;

FIG. 6 is a block diagram illustrating an example of a rear-stage image processing circuit of the frame sequential system;

FIG. 7 is a block diagram illustrating an example of the rear-stage image processing circuit of a simultaneous system;

FIGS. 10 and 11 concern a fourth embodiment of the present invention, in which

FIG. 10 is a diagram schematically illustrating an external appearance of the endoscope apparatus;

FIG. 11 is a block diagram illustrating the output portion of the video ultrasonic observing apparatus;

FIGS. 12 to 16 illustrate a fifth embodiment of the present invention, in which

FIG. 12 is a block diagram illustrating a configuration of the endoscope apparatus;

FIG. 13 is a diagram schematically illustrating an external appearance of the endoscope apparatus;

FIG. 14 is a diagram of a solid-state imaging device;

FIG. 15(A) is a timing chart illustrating an ultrasonic probe driving pulse;

FIG. 15(B) is a timing chart illustrating a vertical register clock pulse supplied to a CCD;

FIG. 15(C) is a timing chart illustrating a horizontal register clock pulse supplied to the CCD;

FIG. 16(A) is a waveform diagram illustrating the ultrasonic probe driving pulse;

FIG. 16(B) is a waveform diagram illustrating a transmitted sound pressure from the ultrasonic probe;

FIG. 16(C) is a waveform diagram illustrating a sound pressure reflected from a living organism;

FIGS. 17, 18(A) and 18(B) relate to a sixth embodiment of the present invention, in which FIG. 17 is a diagram schematically illustrating an arrangement of the endoscope apparatus;

FIG. 18(A) is a flowchart illustrating the operation of the endoscope apparatus in cases where a moving image of an optical image is observed; and FIG. 18(B) is a flowchart illustrating the operation of the endoscope in cases where a moving image of an ultrasonic image is observed.

DESCRIPTION OF THE PREFERRED EMBODIMENTS

Figure 1:
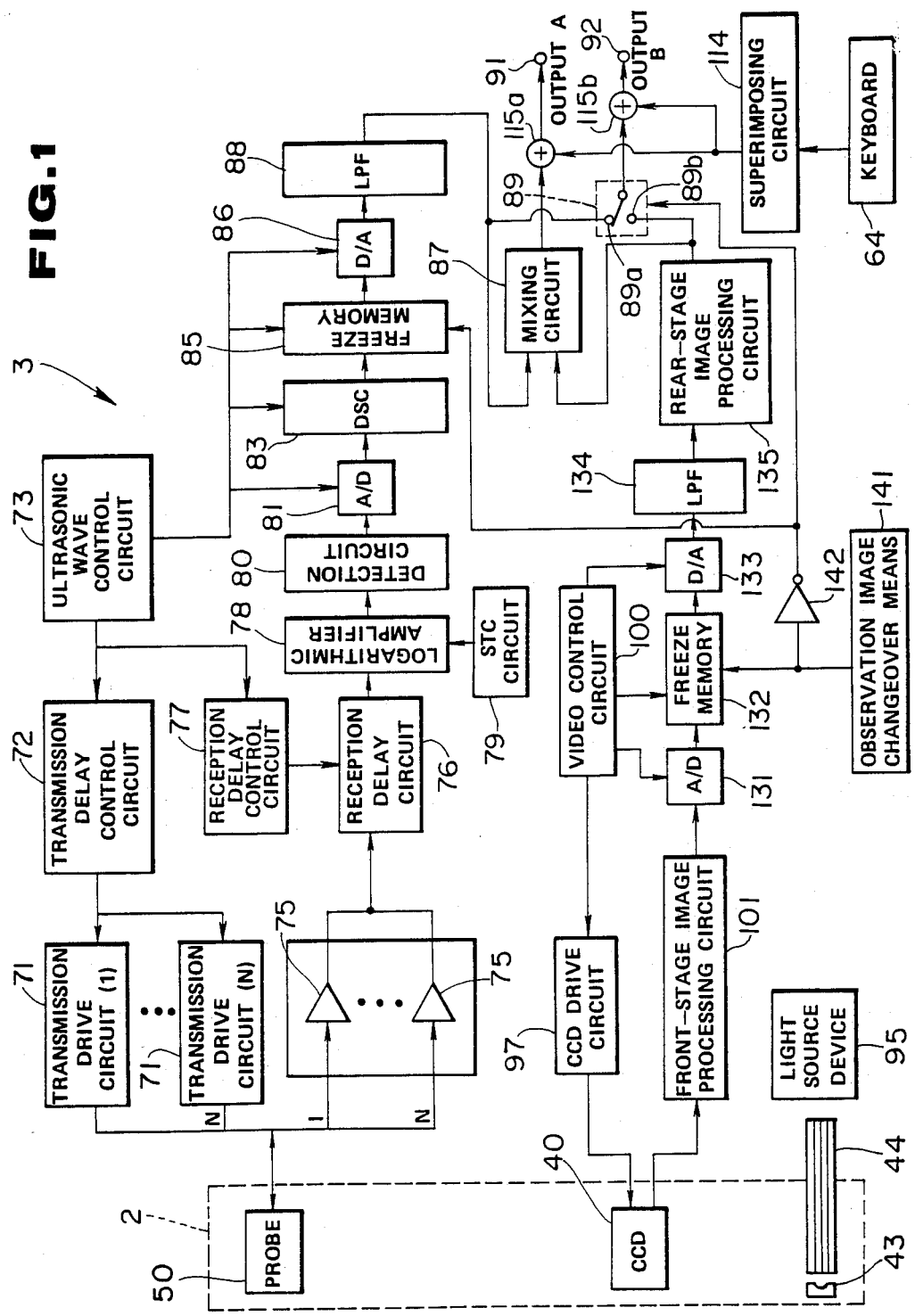
Figure 2:
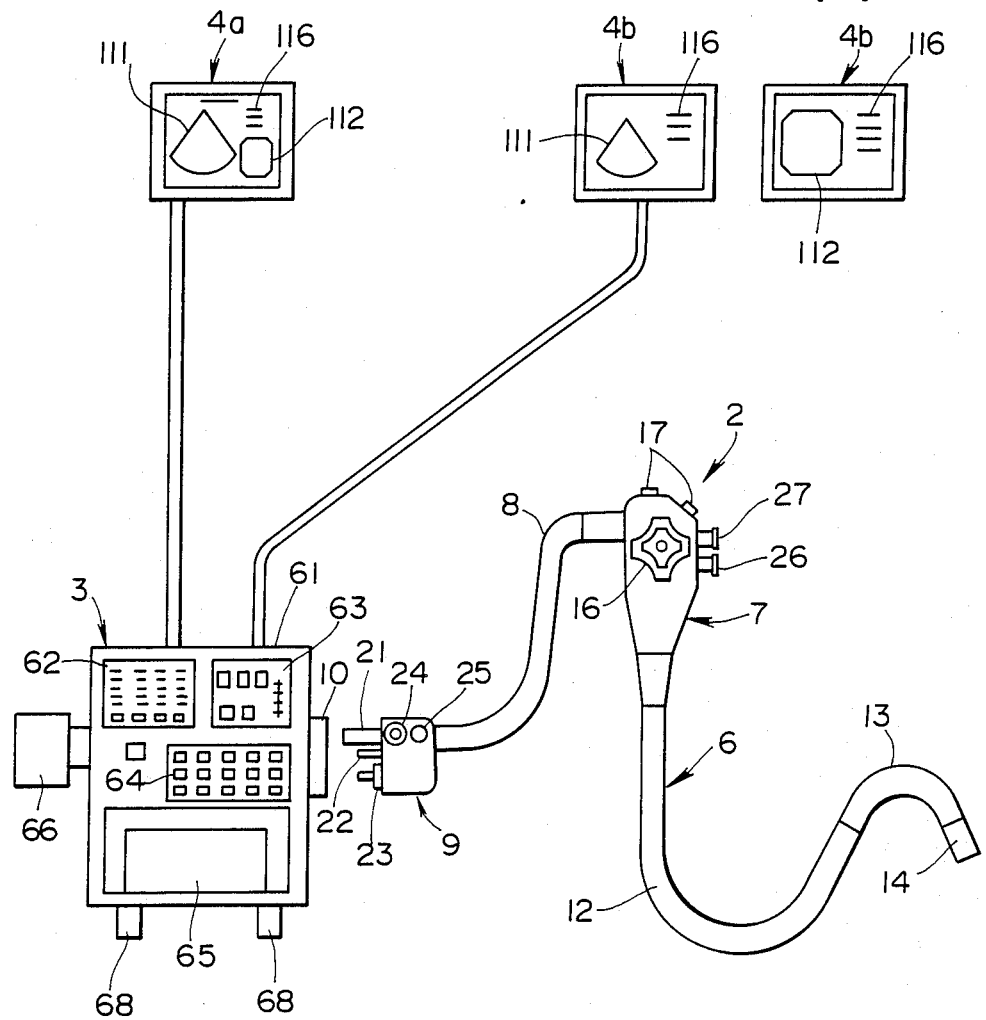

FIGS. 1 to 7 illustrate a first embodiment of the present invention.

As illustrated in FIG. 2(A), an endoscope apparatus 1 comprises a video ultrasonic scope 2, a video ultrasonic observing apparatus 3 to which the video ultrasonic scope 2 is connected, and, say, two observation monitors 4a, 4b connected to the video ultrasonic observing apparatus 3 and serving as the display means.

The video ultrasonic scope 2 has an elongated, and, for instance, flexible inserting section 6, and a large-diameter operating section 7 is connected to a rear end of this inserting section 6. A flexible universal cord 8 extends laterally from a rear end portion of the operating section 7, and a connector 9 is provided at a distal end portion of this universal cord 8. This connector 9 is adapted to be connectable to a connector receptacle 10 which is disposed on, for example, a side portion of the aforementioned video ultrasonic observing apparatus 3.

The inserting section 6 comprises a flexible portion 12 provided on the side of the operating section 7, a curvable bending portion 13 connected to a distal end of this flexible portion 12, and a hard distal end portion 14 connected to a distal end of this bending portion 13. In addition, a bending operation knob 16 is provided in the operating section 7, and the bending portion 13 can be bent vertically or horizontally as the bending operation knob 16 is turned. In addition, a remote switch 17 for, for example, freezing an image being observed is provided at a rear end portion of the operating section 7.

The connector 9 is arranged such that an illumination system connector 21, an air-feeding system connector 22, and an electrical system connector 23 are integrally formed. A water feeding plug 24 and a suction plug 25 are provided on a side of this connector 9. An air/water feeding channel communicating with the air-feeding-system connector 22 and the water feeding plug 24 as well as a suction channel communicating with the suction plug 25 are provided from this connector 9 to the distal end portion 14 through the universal cord 8, the operating section 7, and the inserting section 6. In addition, the operating section 7 is provided with an air/water feeding button 26 for feeding air and water as well as a suction button 27 for sucking.

Figure 3:
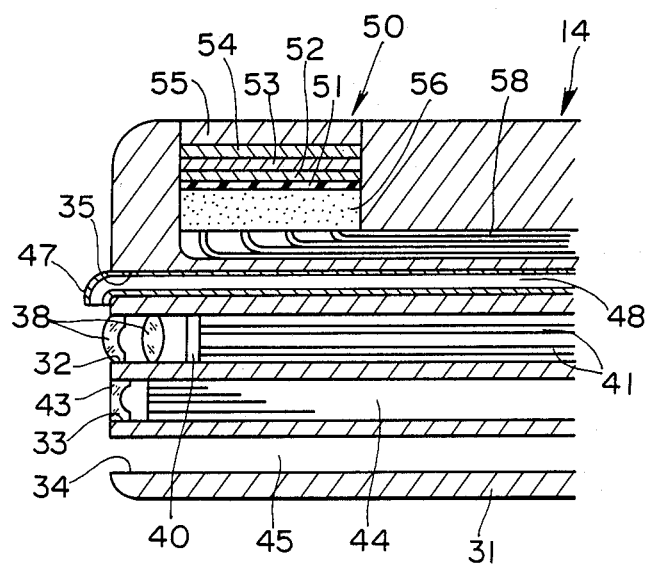

The distal end section 14 is arranged as shown in FIG. 3.

Namely, the distal end portion 14 has a substantially cylindrically-shaped distal end portion body 31 made of a hard material such as a metal. An observation through hole 32 is formed in the vicinity of a central axis of the distal end portion body 31 such as to penetrate the same in parallel with the axial direction of the inserting section 6. An illumination through hole 33 and a suction-channel through hole 34 are formed on one side of this observation through hole 32, while an air/water-feeding-channel through hole 35 is formed on the other side of the observation through hole 32 such as to be adjacent to this observation through hole 32. In addition, an ultrasonic probe 50 serving as a means for obtaining an ultrasonic image and exposed on a side portion of the distal end portion 14 is disposed on an outer peripheral side of this air/water-feeding-channel through hole 35.

An objective lens system 38 is installed at the distal end of the observation through hole 32, and a solid-state imaging device as an imaging means for obtaining an optical image, e.g., a CCD 40, is disposed at an image-forming position of this objective lens system 38. A signal cable 41 is connected to this CCD 40, is inserted through the inserting section 6 and the universal cord 8 and is connected to the electrical system connector 23 of the connector 9. In addition, a light distribution lens 43 is installed at a distal end side of the illumination through hole 33, while a light guide fiber 44 is disposed at a rear end side of this light distribution lens 43. This light guide fiber 44 is inserted through the inserting section 6 and the universal cord 8, and is connected to the illumination system connector 21 of the connector 9. Furthermore, a suction channel tube (not shown) for defining a suction channel 45 is connected to the suction channel through hole 34, is inserted through the inserting section 6 and the universal cord 8, and is connected to the suction plug 25 of the connector 9. An air/water feeding nozzle 47 which is open on a distal end side of the objective lens system 38 is provided in the air/water-feeding-channel through hole 35. An air/water-feeding-channel tube (not shown) for defining a air/water feeding channel 48 is connected to this air/water feeding nozzle 47. This air/water-feeding-channel tube is inserted through the inserting section 6 and the universal cord 8, and is connected to the air/water feeding plug 24 of the connector 9.

The ultrasonic probe 50 has a vibrator 52 which is provided on a flexible substrate 51 and is adapted to generate an ultrasonic pulse. An acoustic lens 55 is provided on this vibrator 52 via a first alignment layer 53 and a second alignment layer 54. This acoustic lens 55 is exposed on an outer peripheral portion of the distal end portion 14. The acoustic lens 55 has functions of insulating and protecting the human body and protecting the vibrator 52. In addition, if its material and configuration are selected appropriately, it is possible to converge ultrasonic waves by making use of the refraction of the sound. The first and second alignment layers 53, 54 are provided to align ultrasonic waves so that the ultrasonic waves will smoothly enter the inside of the human body. A damper layer 56 is provided on a rear surface of the flexible substrate 51. This damper layer 56 has the function of causing vibrational energy enclosed in the vibrator 52 to be dissipated quickly and of preventing the width of the ultrasonic pulse from becoming large. In addition, a signal cable 58 is connected to the flexible substrate 51, is inserted through the universal cord 8, and is connected to the electrical system connector 23 of the connector 9.

Meanwhile, the video ultrasonic observing apparatus 3 is arranged such that a signal processing means for processing signals for the CCD 40, a signal processing means for processing signals for the ultrasonic probe 50, and a light source for supplying illumination light for obtaining an optical image are integrally accommodated in a housing 61. As the connector 9 of the video ultrasonic scope 2 is connected to the connector receptacle provided on, for instance, a side portion of the housing 61, the CCD 40 and the ultrasonic probe 50 inside this video ultrasonic scope 2 are connected to the respective signal processing means, and the light guide fiber 44 is connected to the light source.

A video controller 62 for operating an optical image formed by the CCD 40 and an ultrasonic controller 63 for operating an ultrasonic image formed by the ultrasonic probe 50 are respectively arranged on the left- and right-hand sides on, for instance, a front surface of the housing 61. Disposed therebelow is a common keyboard 64 which is capable of operating the optical image as well as the ultrasonic image. In addition, an external memory apparatus 65, such as a video tape recorder, is capable of being accommodated below the keyboard 64. An external recording apparatus 66 such as a Polaroid (brand name) camera and a printer is adapted to be installed on a side of the housing 61. Incidentally, castors 68 are provided on the housing 61 so that it can be moved.

The internal configuration of the video ultrasonic observing apparatus 3 is shown in FIG. 1.

In this embodiment, an example is shown in which a sector electronic scanning system is used as the signal processing means for obtaining an ultrasonic image.

In the case of the sector electronic scanning system, a multiplicity of, e.g., an N number of, vibrating element groups are provided as the vibrator 52 of the ultrasonic probe 50. When the video ultrasonic scope 2 and the video ultrasonic observing apparatus are connected to each other, transmission drive circuits 71 for exciting the vibrating elements are respectively connected to the vibrating elements of the vibrating element group. For instance, an N number of these transmission drive circuits 71 are provided in correspondence with the number of the vibrating elements. Each of the transmission drive circuits 71 is adapted to be operated with a predetermined time lag by a transmission delay control circuit 72 which is controlled by an ultrasonic control circuit 73. As the time lag is made to vary consecutively, an ultrasonic beam generated from the ultrasonic probe 50 is made to scan in the shape of a fan. The ultrasonic control circuit 73 is controllable by the ultrasonic controller 63 disposed on the front surface of the housing 61.

Ultrasonic waves generated by the ultrasonic probe 50 are transmitted to the interior of the body, are reflected by boundaries or the like inside the intracorporeal tissue, return to the ultrasonic probe 50 as an echo, and are then converted into an electrical signal by the vibrator 52. Electrical signals from the vibrating elements of the vibrator 52 are respectively amplified by preamplifiers 75 and are then input to a reception delay circuit 76. As for the preamplifiers 75, for example, an N number of them are provided in correspondence with the number of the vibrating elements. Ultrasonic echoes from an identical region of the body reach the vibrating elements at different times. The reception delay circuit 76 is so arranged that an amount of delay is controlled by a reception delay control circuit 77 which is in turn controlled by the ultrasonic control circuit 73, and that the phases of ultrasonic echo signals with respect to an identical region are aligned as the ultrasonic echo signals from the respective vibrating elements are delayed by different amounts of delay. The ultrasonic cho signals from the reception delay circuit 76 are input to a logarithmic amplifier 78. This logarithmic amplifier 78 logarithmically compresses the dynamic range of the ultrasonic echo signals so as to be capable of boosting a wide range of ultrasonic echo signals without distortion. In addition, the ultrasonic echo signals are subjected to logarithmic compression by the logarithmic amplifier 78, and the sensitivity thereof is compensated by a sensitivity time control (STC) circuit 79. Namely, since ultrasonic waves attenuate while being propagated through the living organ, the STC circuit 79 compensates the sensitivity with respect to the distance of propagation of ultrasonic waves so that there will be no difference in the magnitude of echoes resulting from the attenuation and that an image will be displayed with a fixed degree of brightness. The ultrasonic echo signal subjected to logarithmic compression by the logarithmic amplifier 78 is input to a detection circuit 80 and is detected by the same so as to be converted into an envelope signal (also referred to as the "A mode signal"). This A mode signal is converted into a digital signal by an A/D converter 81 and is input to a digital scan converter (hereafter referred to as the "DSC") 83. This DSC 83 stores the A mode signal as a digital amount and is read as a television video signal so as to be displayed in a B mode, for instance. The digital video signal read from the DSC circuit 83 is input to a freeze memory 85 constituted by a frame memory. When the writing in this freeze memory 85 is prohibited, the ultrasonic image can be made into a still image. An output signal of this freeze memory 85 is converted into an analog video signal by a D/A converter 86, and this analog video signal is passed through a low-pass filter 88 for overcoming the discontinuity of the signal occurring during such as D/A conversion. Subsequently, the analog video signal is input to a mixing circuit 87 and is then input to one changeover contact 89a of a two-contact changeover switch 89. The video signal output from the mixing circuit 87 is output as one output A from an output terminal 91. This output A is input to one observation monitor 4a. In addition, the video signal output from a fixed contact of the changeover switch 89 is output from an output terminal 92 as the other output B. This output B is input to the other observation monitor 4B.

The ultrasonic control circuit 73 applies clock pulses to the A/D converter 81 and the D/A converter 86 as well as address, write and read signals to the DSC 83 and the freeze memory 85 so as to control them.

Meanwhile, in order to obtain an optical image, a light source 95 is provided in the video ultrasonic observing apparatus 3. If the frame sequential system is used as a color imaging system, this light source 95 is disposed on the front surface side of the light source lamp and is provided with a rotary color filter having color transmissive filters of various colors of red (R), green (G) and blue (B) and rotated by a motor. Illumination light which is made emergent from the light source lamp is consecutively converted into light having various wavelengths of R, G and B and is then condensed by a condenser lens before being made incident upon the incident end of the light guide fiber 44 of the video ultrasonic scope 2 connected to the video ultrasonic observing apparatus 3. On the other hand, if the simultaneous system is used as the color imaging system, white light made emergent from a white light source is made incident upon the incident end of the light guide fiber. This illumination light is led to the distal end portion 14 via the light guide fiber 44, is made emergent from the emergent end, and is radiated to the object via the light distribution lens 43.

An image of the image radiated by the illumination light is formed on the CCD 40 by means of the objective lens system 38. This CCD 40 is to be driven by a CCD drive circuit 97 provided in the video ultrasonic observing apparatus 3. As for the CCD drive circuit 97, the timing of various pulse signals is controlled by a drive signal supplied from a video control circuit 100. The signal read from the CCD 40 is input to a front-stage image processing circuit 101.

Figure 4:
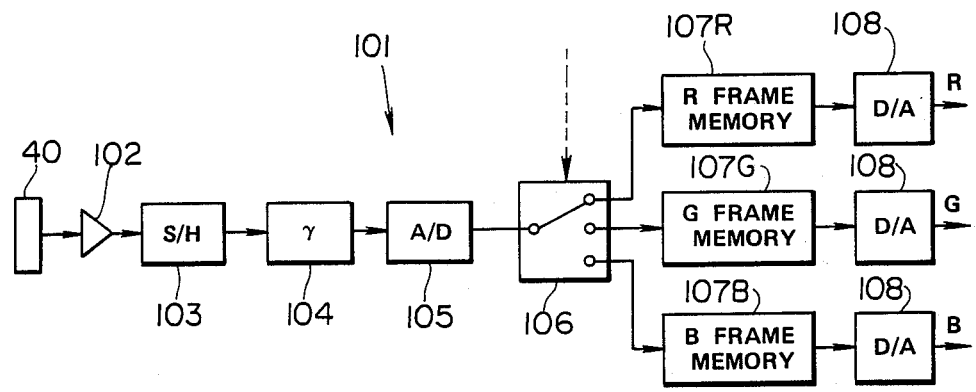

In the case of the frame sequential system, the front-stage image processing circuit 101 is configured as shown in FIG. 4. Namely, the signal read from the CCD 40 is amplified by a preamplifier 102, and a video signal is subsequently extracted in a sample-hold circuit 103, and is subjected to γ-compensation in a γ-compensation circuit 104. This video signal is then converted into a digital signal by an A/D converter 105 and is supplied to a multiplexer 106 which changes over the signal consecutively into signals of various color components in synchronism with frame sequential illumination. These signals are stored consecutively in frame memories 107R, 107G and 107B corresponding to the respective colors of R, G and B. The signals stored in the frame memories 107R, 107G and 107B are read out simultaneously, and are respectively converted into analog chrominance signals by D/A converters 108.

Figure 5:
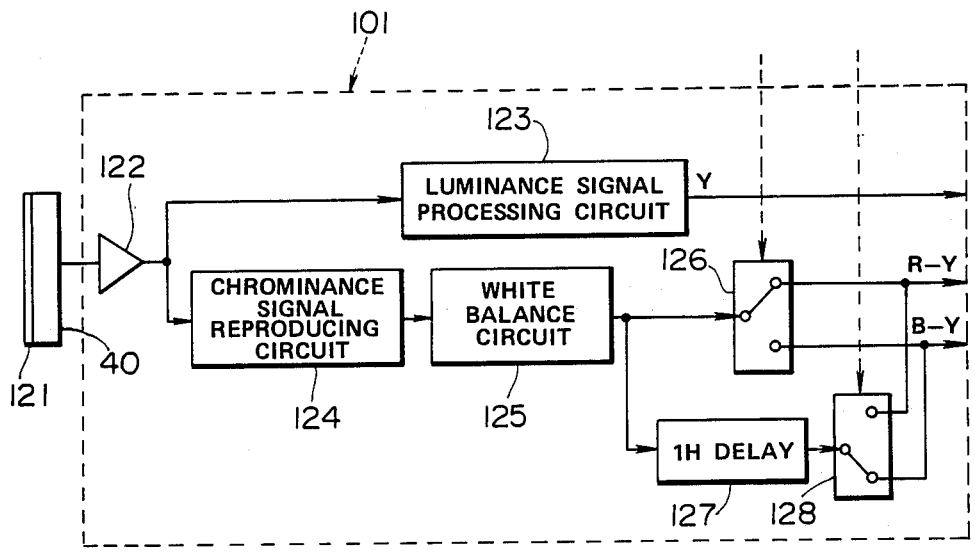

For a simultaneous system, the front-stage image processing circuit 101 is configured as shown in FIG. 5, for example. Namely, a color filter array 121, in which color filters which are capable of transmitting the light of the respective color components of R, G and B are arranged in the form of a mozaic, is provided in front of the CCD 40. The signal read from the CCD 40 is amplified by a preamplifier 122 and is input to a luminance signal processing circuit 123 and a chrominance signal reproducing circuit 124. A luminance signal Y is generated in the luminance signal processing circuit 123. In addition, color difference signals R - Y, B - Y are generated in the chrominance signal reproducing circuit 124 in the manner of a time series for each horizontal line, and compensation of white balance is achieved in a white balance circuit 125. Subsequently, one set of the signals are input directly to an analog switch 126, while the other set are input to an analog switch 128 via a 1 H delay line 127 where they are delayed by one horizontal line. Thus the chrominance signals R - Y, B- Y are obtained by the analog switches 126, 128.

The video signal output from the front-stage image processing circuit 101 is converted into a digital signal by an A/D converter 131, and is input to a freeze memory 132 constituted by a frame memory. As writing in this freeze memory 132 is prohibited, an optical image can be made into a still image. The output signal of this freeze memory 132 is converted into an analog video signal by a D/A converter 133, and this analog video signal is passed through a low-pass filter 134 for overcoming the discontinuity of the signal occurring during such as D/A conversion. Subsequently, the analog video signal is input to a rear-stage image processing circuit 135.

The video control circuit 100 applies clock pulses to the A/D converter 131 and the D/A converter 133 as well as address, write and read signals to the freeze memory 132 so as to control them.

Figure 6:
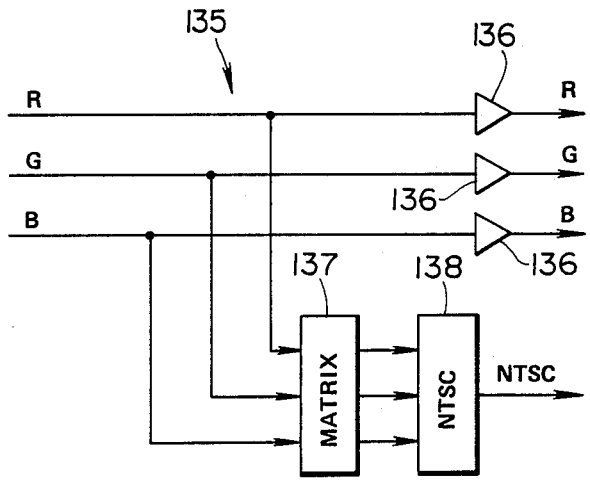

For a frame sequential system, the rear-stage image processing circuit 135 is configured as shown in FIG. 6. Namely, the chrominance signals R, G, B are respectively output as the three primary color signals via drivers 136. In addition, the chrominance signals R, G, B are also delivered to a matrix circuit 137 where the luminance signal Y and the color difference signals R - Y, B - Y are generated and are then input to an NTSC encoder 138 where they are converted into and output as a composite video signal of the NTSC system.

Figure 7:
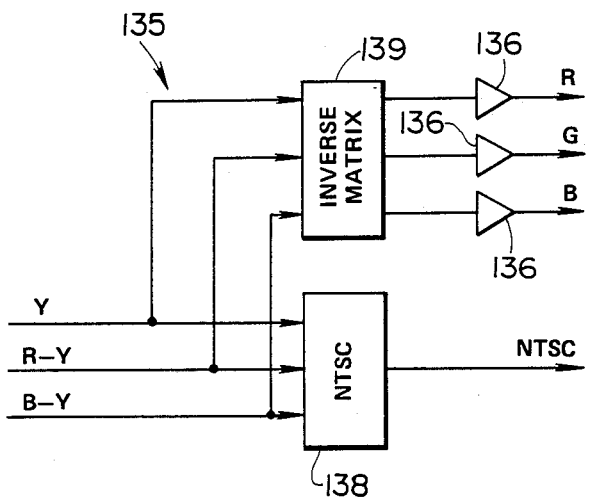

Meanwhile, for simultaneous system, the rear-stage image processing circuit is configured as shown in FIG. 7. Namely, the luminance signal Y and the color difference signals R - Y, B - Y are input to the NTSC encoder 138, and are converted into and output as a composite video signal of the NTSC system. In addition, the luminance signal Y and the color difference signals R - Y, B - Y are input to an inverse matrix circuit 139 where they are converted into the chrominance signals R, G, B, and are output as the three primary color signals R, G, B via the drivers 136.

The video signal from the post-stage image processing circuit 135 is input to the mixing circuit 87 and is also input to the other changeover contact 89b of the two-contact changeover switch 89. The ultrasonic image and the optical image are synthesized by the mixing circuit 87. As shown in FIG. 2(A), an ultrasonic image 111 and an optical image 112 are displayed on the monitor 4a, to which the output A from the mixing circuit 87 is input, such as to be juxtaposed side by side. Meanwhile, the ultrasonic image 111, shown in FIG. 2(A), or the optical image 112, shown in FIG. 2(B), can be displayed on the monitor 4b, to which the output B from the changeover switch 89 is output, by being changed over in accordance with a changeover by the changeover switch 89.

Meanwhile, the common keyboard 64 is so arranged as to be capable of inputting patient data and the like to the superimposing circuit 114 provided in the video ultrasonic observing apparatus 3. Mixers 115a, 115b for mixing the output of the superimposing circuit 114 and the video signal are respectively interposed between the mixing circuit 89 and an output terminal 91 and between the changeover switch 89 and an output terminal 92. The patient data and the like input by means of the keyboard 64 are adapted to be displayed on the screens of the monitors 4a, 4b through superimposition by means of the superimposing circuit 114 and the mixers 115a, 115b. In FIGS. 2(A) and 2(B), reference numeral 116 denotes the patient data and the like displayed on the monitors 4a, 4b.

In this embodiment, an observation image changeover means 141 is provided for selecting an image to be viewed as a moving image as between the ultrasonic image and the optical image. This observation image changeover means 141 is adapted to apply a freeze signal to the freeze memory 85 for freezing the ultrasonic image via an inverter 142 and to the freeze memory 132 for freezing the optical image, respectively, so as to directly prohibit writing therein and to freeze the images. Furthermore, the freeze signal which has passed through the inverter 142 also serves as a changeover signal for controlling the changeover by the changeover switch 89. For example, the freeze memories 85, 132 are frozen when the freeze signals are at the H level. In addition, when the changeover signal is at the H level, the changeover terminal 89b of the changeover switch 89 on the optical image side assumes a connected state, while, when the changeover signal is at the L level, the changeover terminal 89a on the ultrasonic image side assumes a connected state.

When an ultrasonic image is viewed, the H-level signal is output from the observation image changeover means 141, so that the ultrasonic image-side freeze memory 85 does not undergo a freezing operation, while the optical image-side freeze memory 132 undergoes a freezing operation. In addition, as for the changeover switch 89, the ultrasonic image-side changeover terminal 89a assumes a connected state. In this case, the moving ultrasonic image 111 and the still optical image 112 are displayed on one monitor 4a, while the moving ultrasonic image 111 is displayed on the other monitor 4b, as shown in FIG. 2(A).

Meanwhile, when an optical image is viewed, the L-level signal is output from the observation image changeover means 141, and the ultrasonic image-side freeze memory 85 undergoes a freezing operation, while the optical image-side freeze memory 132 does not undergo a freezing operation. In addition, as for the changeover switch 89, the optical image-side changeover terminal 89b assumes a connected state. In this case, the still ultrasonic image 111 and the moving optical image 112 are displayed on one monitor 4a, while the moving optical image 112 is displayed on the other monitor 4b, as shown in FIG. 2(B).

Thus, in this embodiment, there are provided the freeze memory for freezing the ultrasonic image and the freeze memory 132 for freezing the optical image, and as the image to be observed is changed over by means of the observation image changeover means 141, one of the freeze memories 85, 132 is adapted to undergo a freezing operation.

Accordingly, when an ultrasonic image is viewed, the optical image is frozen, whereas, when an optical image is viewed, the ultrasonic image is frozen to the contrary.

Thus, since it is possible to view one of the ultrasonic image and the optical image as a still image while the other image is being viewed as a moving image, it is possible to correlate the ultrasonic image with the optical image. In addition, when the ultrasonic image is being viewed, it becomes possible to ascertain a region being observed.

Also, when one of the ultrasonic image and the optical image is being viewed as a moving image, not the image obtained by driving the CCD 40 or the ultrasonic probe 50 but one stored in the freeze memory 85 or 132 is displayed as the other image. Accordingly, it becomes less frequent for signals for obtaining an image being viewed to be mixed in the other image, so that it is possible to view the other image with a small amount of noise.

In addition, the observation image changeover means 141 may be provided not on the side of the video ultrasonic observing apparatus 3 but, for instance, in the operating section 7 of the video ultrasonic scope 2.

The changeover of the changeover switch 89 may be reversed, and an arrangement may be provided such that a still image is displayed on the monitor 4b.

An arrangement may be alternately provided such that observation is effected only by the monitor 4a on which the ultrasonic image and the optical image are displayed, without providing the monitor 4b.

When both the ultrasonic and optical images are displayed on the monitor 4a, display may be effected by using a large parent screen and a small child screen. In this case, either of the ultrasonic image and the optical image may used for the parent screen. In addition, either of the parent screen and the child screen may be used as the image to be frozen.

Also, an arrangement may be provided such that the ultrasonic image and the optical image are frozen consecutively or simultaneously.

In addition, an arrangement may be provided such that, by making it possible to suspend the freezing function of the freeze memories 85, 132, when the presence of noise is allowed, both the ultrasonic image and the optical image are displayed as moving images.

Figure 8:
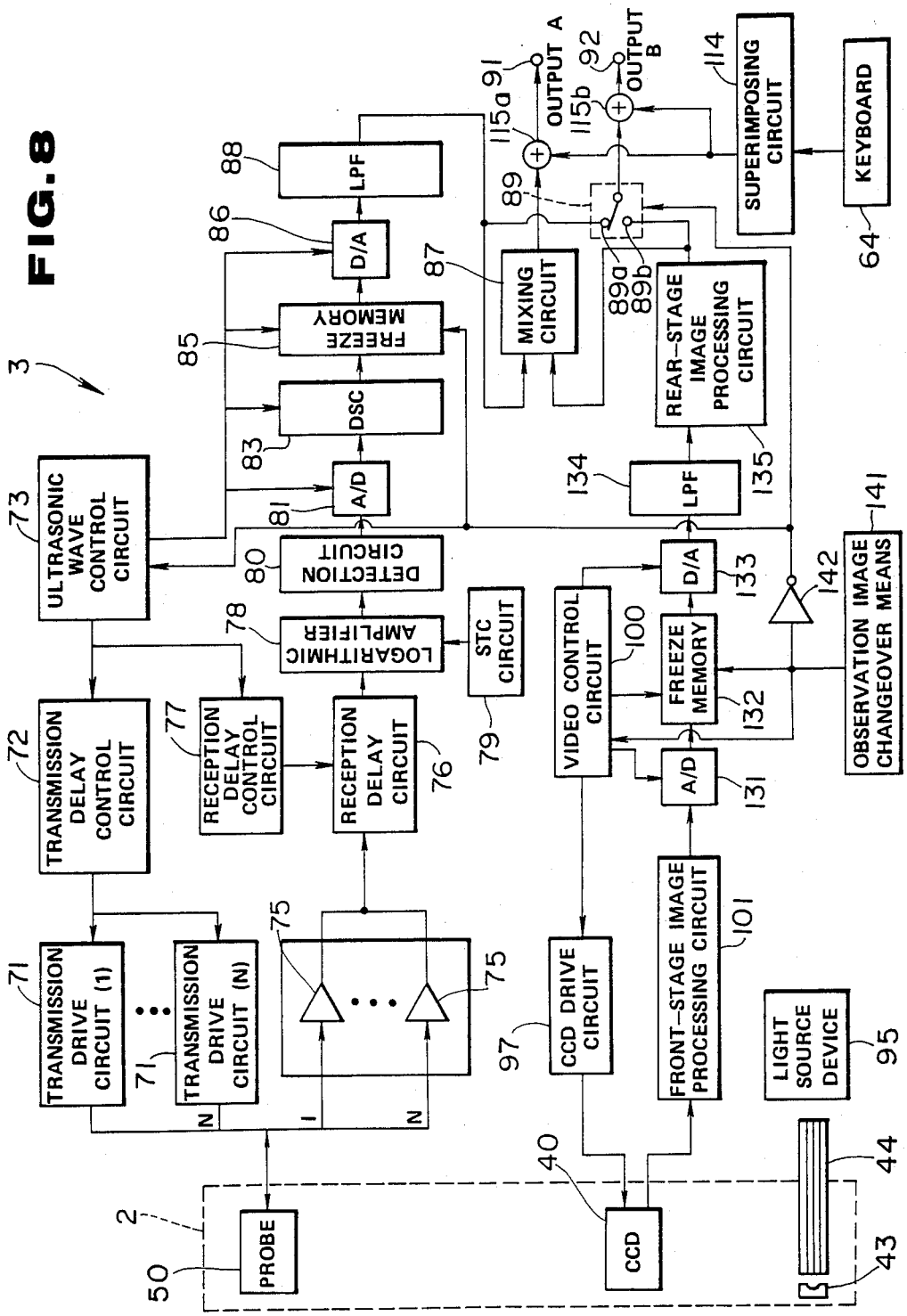
FIG. 8 is a block diagram illustrating a configuration of the endoscope apparatus in accordance with a second embodiment of the present invention.

FIG. 8 illustrates a second embodiment of the present invention.

In this embodiment, the freeze signal output from the observation image changeover means 141 via the inverter 142 is also input to the ultrasonic control circuit 73. In addition, the freeze signal output from the observation image changeover means 141 is directly input to the video control circuit 100. The ultrasonic control circuit 73 is adapted to stop the driving of the ultrasonic probe 50 when the freeze memory 85 effects a freezing operation in response to the freeze signal. Meanwhile, the video control circuit 100 is adapted to stop the driving of the CCD 40 when the memory 132 effects a freezing operation in response to the freezing signal.

In accordance with this embodiment, at the time of viewing the ultrasonic image, the freeze memory 132 effects a freezing operation, and the optical image is frozen, while the driving of the CCD 40 is stopped. Meanwhile, at the time of viewing the optical image, the freeze memory 85 effects a freezing operation, and the ultrasonic image becomes frozen, and the driving of the ultrasonic probe 50 is stopped.

Accordingly, it is possible to more positively obtain an optical image which has a less amount of noise.

The other arrangements, operation and effects are the same as those of the first embodiment.

Figure 9:
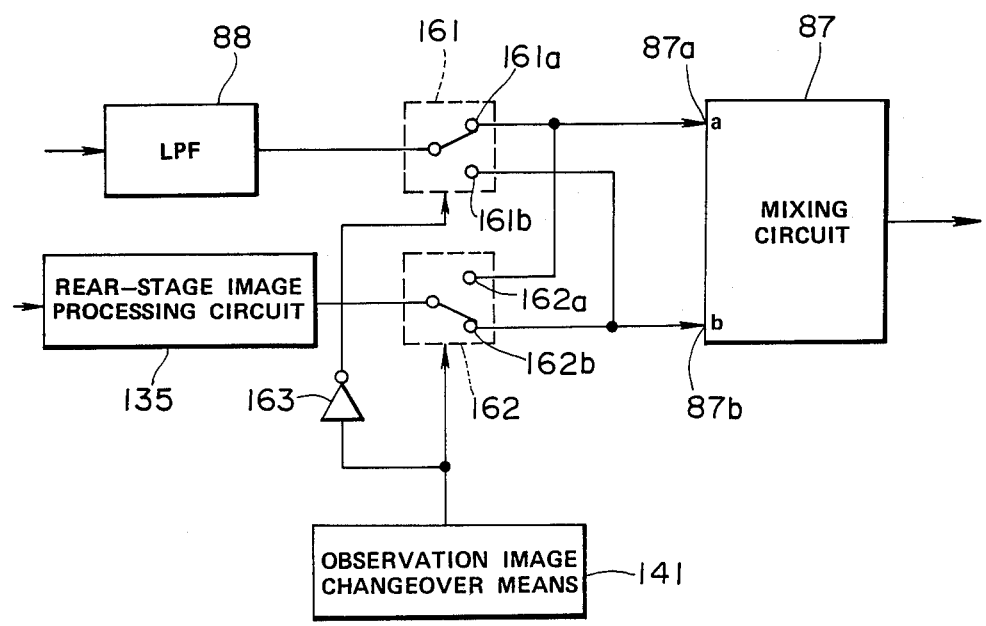
FIG. 9 is a block diagram illustrating an output portion of a video ultrasonic observing apparatus in accordance with a third embodiment of the present invention.

FIG. 9 illustrates a third embodiment of the present invention.

In this embodiment, the arrangement is such that the video signal of the ultrasonic image from the low-pass filter 99 is input to a one-input, two-output changeover switch 161, while the video signal of the optical image from the rear-stage image processing circuit 135 is input to one-input, two-output changeover switch 162. One output terminal 161a of the changeover switch 161 is connected one input terminal 87a of the mixing circuit 87, while the other output terminal 161b is connected to the other input terminal 87b. Similarly, one input terminal 162a of the changeover switch 162 is connected to one input terminal 87a of the mixing circuit 87, while the other output terminal 162b is connected to the other input terminal 87b of the mixing circuit 87.

The mixing circuit 87 is adapted to mix the video signals in such a manner that the video signal input from the input terminal 87a is displayed on the parent screen and the video signal input from the input terminal 87b on the child screen.

The changeover of the changeover switch 161 is controlled by the freeze signal output from the observation changeover means 141 via the inverter 163, while the changeover of the changeover switch 162 is controlled by the freeze signal directly applied by the observation image changeover means 141. As for the switches 161, 162, the output terminals 161a, 162a assume a connected state when the changeover signal is at the L level, while the output terminals 161b, 162b assume a connected state when the changeover signal is at the H level. Accordingly, when the optical image is frozen, the video signal of the ultrasonic image is input the input terminal 87a of the mixing circuit 87, and the video signal of the optical image is input to the input terminal 87b of the mixing circuit 87. Meanwhile, when the ultrasonic image is frozen, the video signal of the optical image is input to the input terminal 87a of the mixing circuit 87, while the video signal of the ultrasonic image is input to the input terminal 87b of the mixing circuit 87.

Namely, when the optical image is frozen, the moving ultrasonic image is displayed on the parent screen, and the still optical image is displayed on the child screen. Meanwhile, when the ultrasonic image is frozen, the moving optical image is displayed on the parent screen, while the still ultrasonic image is displayed on the child screen.

Thus, in this embodiment, the moving image is constantly displayed on the parent screen and the still image is constantly displayed on the child screen. At the time of a freeze, the ultrasonic image and the optical image are replaced with each other.

An arrangement may be provided such that the operation of the changeover switches 161, 162 is reversed, and the still image is displayed on the parent image and the moving image on the child image.

In addition, an arrangement may be provided such that the ultrasonic image and the optical image can be replaced with each other, as desired.

The other arrangements, operation and effects are the same as those of the first embodiment.

Figure 10:
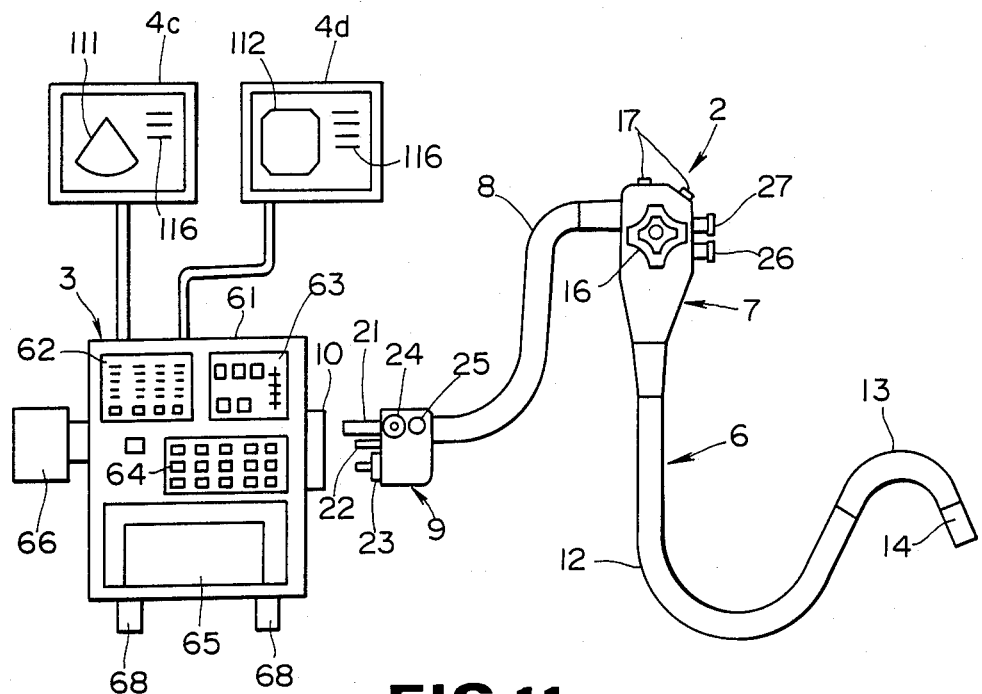
Figure 11:
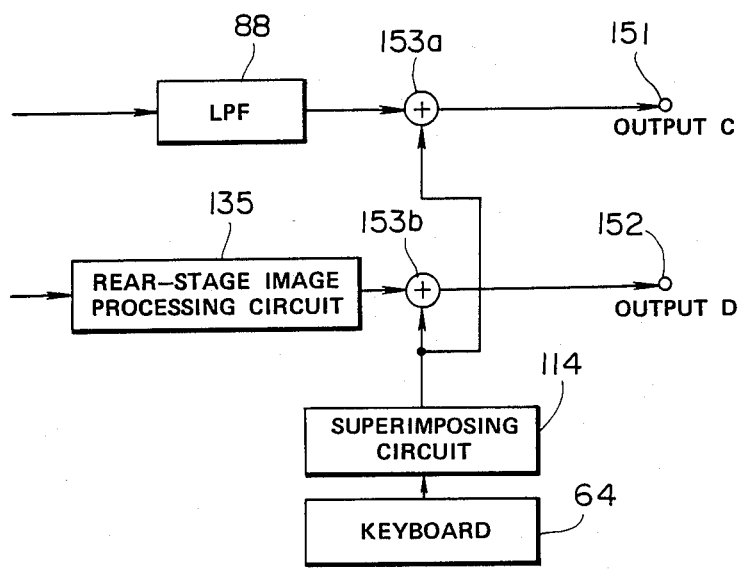

FIGS. 10 and 11 illustrate a fourth embodiment of the present invention.

In this embodiment, as illustrated in FIG. 11, the video signal which has passed through the ultrasonic image-side low-pass filter 88 is output as an output C from an output terminal 151. Meanwhile the video signal from the optical image-side rear-stage image processing circuit 135 is output as an output D from an output terminal 152. As shown in FIG. 10, the output C is input to one monitor 4c, while the output D is input to the other monitor 4d. Incidentally, mixers 153a, 153b for mixing the output of the superimposing circuit 114 and the video signal are respectively interposed between the low-pass filter 88 and the output terminal 151 and between the rear-stage image processing circuit 135 and the output terminal 152. The patient data and the like input by the keyboard 64 are displayed in the images on the monitors 4c, 4c through superimposition by means of the superimposing circuit 114 and the mixers 153a, 153b.

The other arrangements are the same as the first embodiment.

In this embodiment, the ultrasonic image 111 is displayed on the monitor 4c, while the optical image is displayed on the monitor 4d. Furthermore, at the time of observation of the ultrasonic image 111, the optical image 112 is frozen by the observation image changeover means 141, as in the case with the first embodiment, during the observation of the ultrasonic image 111. On the contrary, during the observation of the optical image 112, the ultrasonic image 111 is frozen.

The other operation and effects are the same as those of the first embodiment.

FIGS. 12 to 16 illustrate a fifth embodiment of the present invention.

Figure 13:
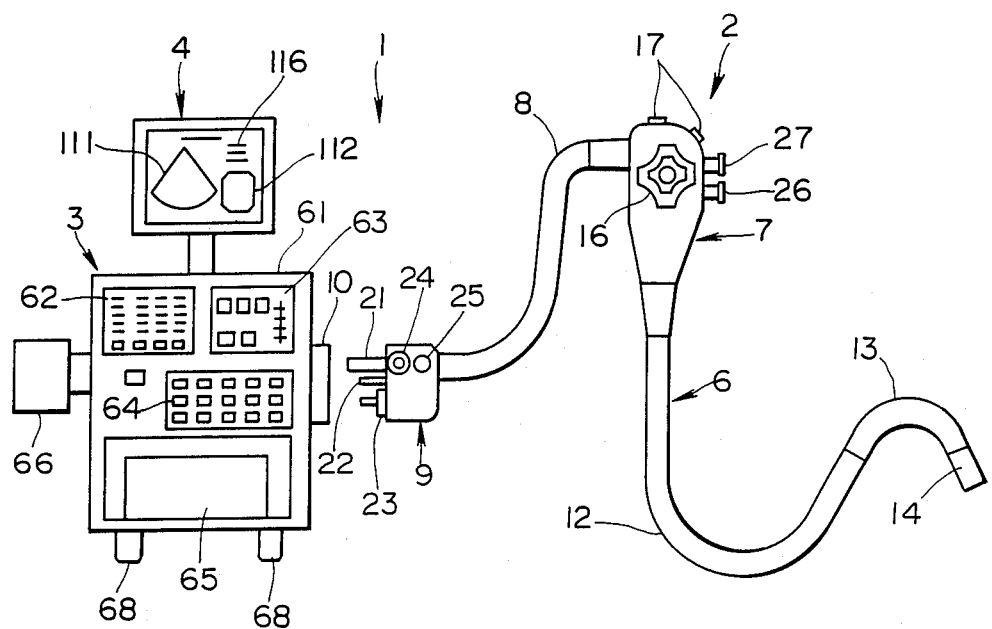

As illustrated in FIG. 13, in this embodiment, one monitor 4 is connected to the video ultrasonic observing apparatus 3.

Figure 12:
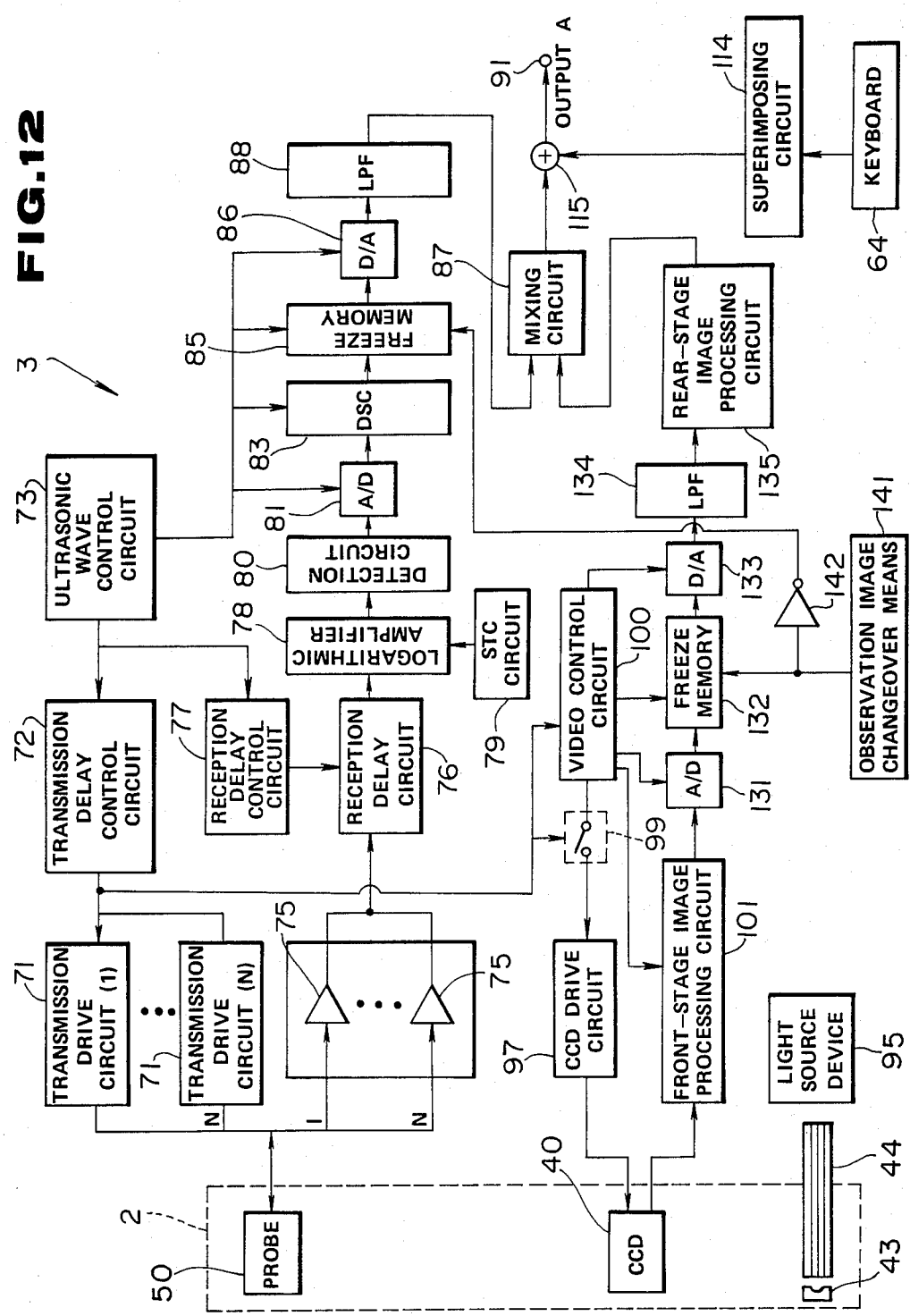

An internal configuration of the video ultrasonic observing apparatus 3 is shown in FIG. 12.

A switch 99 is provided between the video control circuit 100 and a CCD drive circuit 97. A pulse sent from the transmission delay control circuit 72 is adapted to be applied to the switch 99 as a changeover signal so as to output an ultrasonic pulse for operating the transmission drive circuit 71. Namely, when the pulse is output from the transmission delay control circuit 72, the switch 99 is adapted to open only during a period of time when the ultrasonic pulse is sustained. In addition, the pulse transmitted from the transmission delay control circuit 72 is also input to the video control circuit 100. This video control circuit 100 is adapted to stop the operation of the front-stage image processing circuit 101 and the freeze memory 132 when the aforementioned pulse is output.

In addition, in this embodiment, the output of the mixing circuit 87 is mixed with the output of the superimposing circuit 114 by means of the mixer 115, and is output to the monitor 4 from the output terminal 91. As illustrated in FIG. 13, the ultrasonic image 111 and the optical image 112 are adapted to be displayed on the monitor, for instance, side by side. Furthermore, the changeover switch 89, the mixer 115b, and the output terminal 92 in the case of the first embodiment are not provided.

The other arrangements are the same as those of the first embodiment.

As shown in FIGS. 15(A) and 16(B), an ultrasonic probe driving pulse which is applied to the vibrator 52 of the ultrasonic probe 50 has, for instance, a pulse duration of 1 μs, a pulse interval of 300 μs (cycle frequency: approx. 3,300 Hz), and a pulse voltage of 250V. The vibrator 52 vibrates by means of this ultrasonic probe driving pulse, and this vibration, i.e., ultrasonic wave, is transmitted to the interior of the living organ. As shown in FIG. 16(B), the transmission sound pressure of this ultrasonic wave is, for instance, approx. 250 mV and its pulse width is 1 μs. The pulse interval differs depending on the distance of diagnosis. For instance, when the distance of diagnosis is approx. 25 cm–20 cm, the cycle frequency is approx. 3,000 Hz–4,000 Hz, and the pulse interval is 330 μs–250 μs. In addition, as shown in FIG. 15(A), the ultrasonic probe driving pulse is so arranged that one frame is formed by 500 pulses, and 10 frames are formed per second.

The ultrasonic wave generated by the ultrasonic probe 50 is transmitted to the living organ, is reflected by a boundary or the like in the body tissue, return to the ultrasonic probe 50 as an echo, and is converted into an electrical signal by the vibrator 52. The sound pressure of this echo is several tens of mV, as shown in FIG. 16(C).

As for the CCD 40, as shown in FIG. 14, an exposure region 40a is constituted by a total of 30,000 pixels, including 150 vertical pixels and 200 horizontal pixels. In the drawing, reference numeral 40b denotes one pixel. Signal charges accumulated in the exposure area are transferred to a vertical transfer line an interline transfer system or to an accumulating section a frame transfer system in response to a drive pulse from the CCD drive circuit 97. The signal charges thus transferred are transferred to a horizontal register 40c for each line in response to a vertical register clock pulse φp. The signal charges transferred to the horizontal register 40c are transferred consecutively to an output terminal in response to a horizontal register clock pulse φs.

As shown in FIG. 15(B), the vertical register clock pulse φp has, for instance, a cycle of 33 μs, while, as shown in FIG. 15(C), the horizontal register clock pulse φs is so arranged that 200 pulses are output during two adjacent vertical register clock pulses φp at a cycle of 140 ns in correspondence with the number of horizontal pixels. Although the numbers and waveforms of the vertical and horizontal register clock pulses vary depending on the driving system, e.g., 2-phase, 3-phase, and 4-phase driving, the vertical and horizontal register clock pulses φp, φs are typical representations thereof.

In this embodiment, the pulse delivered from the transmission delay control circuit 72 to operate the transmission drive circuits 71 and output the ultrasonic pulse also serves as a signal for changing over the switch 99 interposed between the video control circuit 100 and the CCD drive circuit 97. Namely, the switch 99 is so arranged as to open for the duration of the ultrasonic pulse, for instance, 1 μs, when the pulse is issued from the transmission delay control circuit 72. While that switch 99 is open, the drive signal is not delivered to the CCD drive circuit 97, and application of various drive signals to the CCD 40 by the CCD drive circuit 97 is stopped. Accordingly, during the pulse duration of the ultrasonic probe driving pulse, shown in FIG. 15(A), application of the vertical register clock pulse op and the horizontal register clock pulse as to the CCD 40 is stopped, and reading of the CCD 40 is stopped.

In addition, the pulse delivered from the transmission delay control circuit 72 to operate the transmission drive circuits 71 and to output the ultrasonic pulse is also input to the video control circuit 100. This video control circuit 100 is adapted to stop the operation of the front-stage image processing circuit 101 and the freeze memory 132 in response to the stopping of reading of the CCD 40 at the time when the ultrasonic probe driving pulse is output.

Thus, in this embodiment, as shown in FIG. 15, during the period when the high-tension ultrasonic probe driving pulse is applied to the ultrasonic probe 50, application of drive pulses such as the vertical register clock pulse op and the horizontal register clock pulse os to the CCD 40 is stopped, so that reading of the CCD 40 is stopped. The ultrasonic probe driving pulse has a very short pulse duration of, for instance, 1 μs, and since the pulse interval is 300 μs, the suspension of reading of the CCD 40 occurs at a rate of 1/300 in terms of time, and the reading of the CCD 40 is delayed by this time, but its effect on the image is very small.

Accordingly, it is possible to view both of the optical image and the ultrasonic image simultaneously without a decrease in the amount of information on the optical image formed by the CCD 40. In addition, since the drive pulse for the ultrasonic probe 50 and the drive pulse for the CCD 40 are not output simultaneously, and the respective signals do not interfere each other, it is possible to obtain an ultrasonic image and an optical image which suffer less noise.

In may be provided separately for the ultrasonic image and the optical image, as in the case of the fourth embodiment.

The other operation and effects of this embodiment are the same as those of the first embodiment.

In the first to fifth embodiments, the scanning system of the ultrasonic probe 50 need not be confined to the sector electronic scanning, but the following systems may be employed: the linear electronic scanning, convex-type sector electronic scanning, linear mechanical scanning, arc mechanical scanning, sector mechanical scanning, and radial mechanical scanning.

Figure 17:
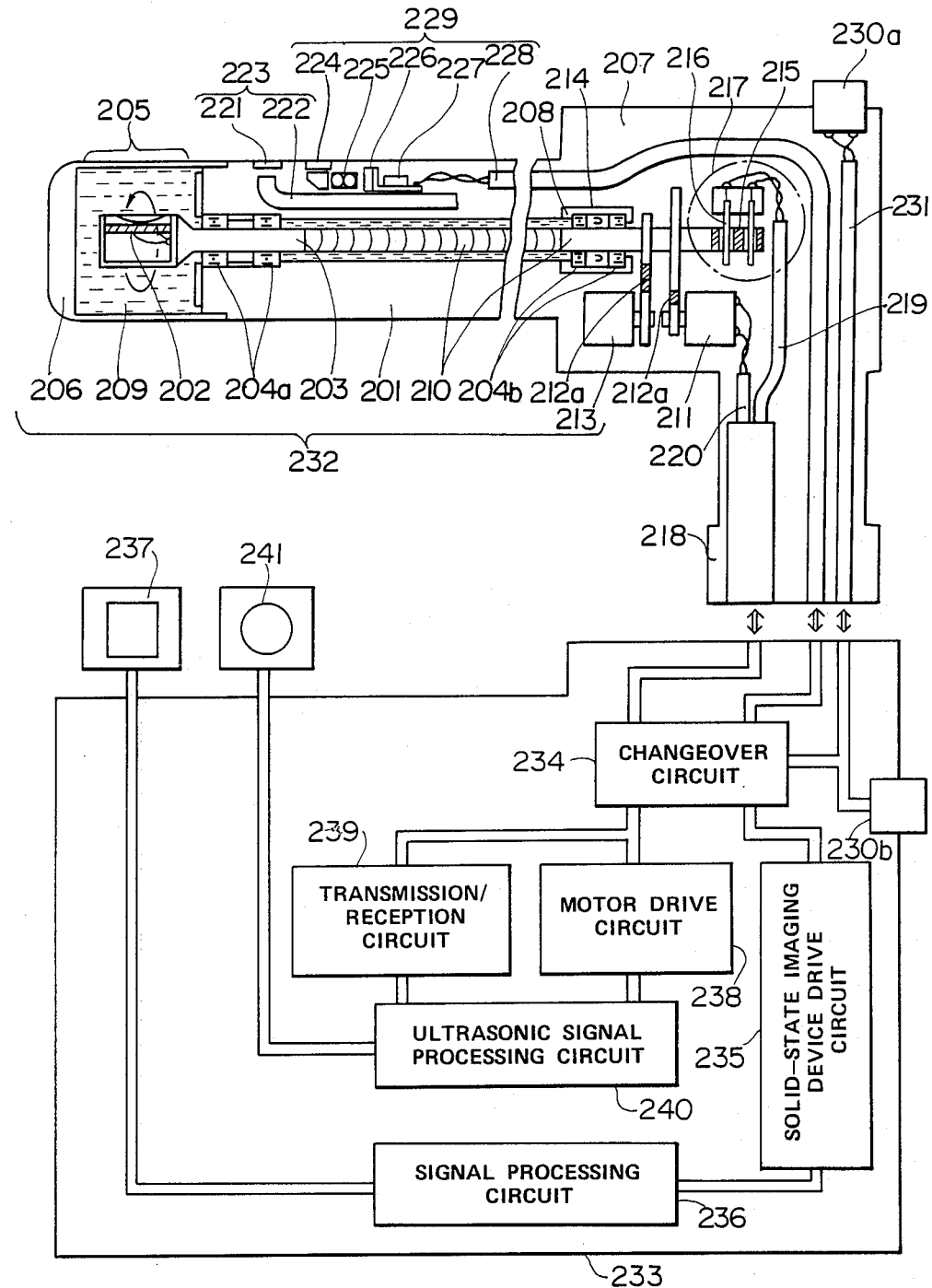

FIGS. 17 and 18 show a sixth embodiment of the present invention.

As shown in FIG. 17, the endoscope apparatus in accordance with this embodiment comprises a video ultrasonic scope 232, a video ultrasonic observing apparatus 233 to which the video ultrasonic scope 232 is connected, and, say, two monitors 237, 241 serving as display means connected to the video ultrasonic observing apparatus 233.

An ultrasonic probe 202 secured to a rotor 203 is provided at a distal end of an inserting section 201 of the video ultrasonic scope 232, and an end cap 206 having a window 205 around the entire rotational periphery thereof is provided thereon. The rotor 203 is provided rotatably via a bearing 204a and is connected to a transmission shaft 210 extending from an operating section 207 through the inserting section 201. An ultrasonic wave transmitting medium 209 is filled in a space around the transmission shaft 210, extending from the inside of the end cap 206 to an oil reservoir portion 208 disposed around an outer periphery of a bearing 204b rotatably supporting the transmission shaft 210 in the operating section 207. Reference numeral 214 denotes a sealant for hermetically sealing the ultrasonic wave transmitting medium 209. The transmission shaft 210 is connected to a drive shaft of a motor 211 via a rotation transmitting member 212a, and is also connected to a rotational position detector (encoder) 213 via a rotation transmitting member 212b. A rotary ring 215 is provided on an end portion of the transmission shaft 210 on the operating section side, and a contact brush 216 is brought into contact with the same so as to constitute a contact member 217, which electrically connects the ultrasonic probe 202 and a signal cable 219 for transmission and reception extending from a connector 218. A drive voltage supplying cable 220 extending from the connector 218 is connected to the motor 211.

The inserting section 201 is provided with an illumination optical system 223 having an illumination lens 221 and a light guide fiber 222, an observation window 224, an objective lens system 225, a solid-state imaging device (CCD) 226, a transistor for driving the solid-state imaging device, electrical parts 227 including a capacitor, and an image transmission unit 229 having a signal cable 228, said light guide fiber 222 and said signal cable 228 extending to the connector 218.

The operating section is provided with a switch 230a for issuing a changeover instruction signal for driving the motor 211 and for driving the solid-state imaging device 226 and is connected to a cable 231 extending from the connector 218.

The video ultrasonic observing apparatus 233 is electrically and mechanically coupled with the video ultrasonic scope 232 via the connector 218. The observing apparatus 233 comprises: a changeover switch 230b; a changeover circuit 234 connected to a changeover switch 230a and the changeover switch 230b; an optical image display system having a solid-state imaging device drive circuit 235, a signal processing circuit 236 and a monitor 237 for displaying an image; and an ultrasonic image display system having a motor drive circuit 238, an ultrasonic wave transmission/reception circuit 239, an ultrasonic signal processing circuit 240, and a monitor 241 for displaying an ultrasonic image. Upon receiving a changeover instruction signal supplied from either of the switches 230a and 230b, the changeover circuit 234 effects changeover between the optical display system and the ultrasonic image system.

In the same way as, for instance, the first embodiment, the signal processing circuit 236 comprises the video control circuit 100, the front-stage image processing circuit 101, the A/D converter 131, the freeze memory 132, the D/A converter 133, the low-pass filter 134, and the rear-stage image processing circuit 135. In addition, in the same way as, for instance, the first embodiment, the ultrasonic signal processing circuit 240 comprises the ultrasonic control circuit 73, the logarithmic amplifier 78, the STC circuit 79, the detection circuit 80, the A/D converter 81, the DSC 83, the freeze memory 85, the D/A converter 86, and the low-pass filter 88.

Since these arrangements are adopted, if the changeover switch 230a, or 230b is set in the state shown in FIG. 18(A), i.e., if the solid-state image driving is set to ON and the driving of the motor 211 is set to OFF, an optical image is displayed on the monitor 237, while a frozen ultrasonic image is displayed on the monitor 241 or the display disappears. Meanwhile, if the changeover switch 230a or 230b is set in the state shown in FIG. 18(B), i.e., if the driving of the motor 211 is set to ON and the driving of the solid-state imaging device is set to OFF, a start pulse is sent from the rotational position detector 213 to the ultrasonic wave transmission/reception circuit 239, transmission and reception with the ultrasonic probe 202 is carried out, and an ultrasonic image is displayed on the monitor 241, while a frozen optical image is displayed on the monitor 237 or the display disappears. Accordingly, it is possible to display a noiseless image on the monitor with which diagnosis of the image is being conducted. In addition, since the changeover switch 230a is provided on the operating section 207, it is possible to operate it simply since it is close at hand, without using the changeover switch 230b provided on the observing apparatus 233.

In this embodiment, although the ultrasonic motor is provided at the distal end of the inserting section and the rotor is driven, an as for the ultrasonic scanning system, a sector scanning system may be used instead of the radial scanning system in which scanning is effected along the entire periphery, or it is also possible to adopt a forward viewing type in which an illumination window and an observation window are provided at the distal end of the inserting section such as to face forwardly. In addition, it is also possible to adopt an arrangement in which display is effected by alternately changing over the optical image and the ultrasonic image on one monitor, or an arrangement in which the optical image displaying system and the ultrasonic image displaying system are not formed integrally and are arranged as two separate systems which are connected to separate connectors coupled with the video ultrasonic scope.

As has been described above, according to this embodiment, it is possible to provide an endoscope apparatus which is capable of making noiseless the image displayed on the monitor by the simple operation of changing over one switch and of making proper diagnosis of the image.

Also, it should be noted that the present invention should not be restricted to the foregoing embodiments, and, for instance, as for the imaging means, a television camera installed in an eyepiece section of a scope which is capable of effecting visual observation, such as a fiberscope, may be used.

The solid-state imaging device is not restricted to the CCD, and a MOS, a CSD, a CPD, or the like may be used.

As many apparently widely different embodiments of this invention may be made without departing from the spirit and scope thereof, it is to be understood that the invention is not limited to the specific embodiments thereof except as defined in the appended claims.

What is claimed is:

1. An endoscope apparatus comprising:
   an endoscope including and elongated inserting section having an illumination window and an observation window at a distal end portion thereof, illuminating means for allowing illumination light to emerge from said illumination window, imaging means for forming an optical image of an object upon receiving light which is radiated through said observation window after being reflected from said object, and an ultrasonic probe disposed at said distal end portion of said inserting and obtaining an ultrasonic image of said object;
   optical-image signal processing means for signal processing for said imaging mean and for generating a video signal of said optical image, said optical-image signal processing means having an optical image memory means for storing said optical image;
   ultrasonic-image signal processing means for processing a signal for said ultrasonic probe and for generating a video signal of said ultrasonic image, said ultrasonic-image signal processing means having an ultrasonic image memory means for storing said ultrasonic image; and
   memory control means for controlling writing and reading by said optical image memory means and said ultrasonic image memory means, for simultaneously outputting a video signal for displaying a moving ultrasonic image and a video signal for displaying a still optical image when a moving ultrasonic image is viewed and for simultaneously outputting a video signal for displaying a moving optical image and a video signal for displaying a still ultrasonic image when a moving optical is viewed.

2. An endoscope apparatus according to claim 1, wherein said optical image memory means and said ultrasonic image memory means are respectively constituted by frame memories.

3. An endoscope apparatus according to claim 2, wherein said memory control means for prohibiting writing in said frame memories in order to display said still optical and still ultrasonic images.

4. An endoscope apparatus according to claim 1, further comprising display means for displaying said optical image and said ultrasonic image as said video signal of said optical image and said video signal of said ultrasonic image are input thereto.

5. An endoscope apparatus according to claim 4, further comprising synthesizing means for synthesizing said video signal of said optical image and said video signal of said ultrasonic image, said display means having a display apparatus to which an output signal of said synthesizing means is input and which displays said optical image and said ultrasonic image on one screen.

6. An endoscope apparatus according to claim 5, further comprising changeover means for outputting either said video signal of said optical image or said video signal of said ultrasonic image by changing over the same, said display means further having a display apparatus to which an output signal of said changeover means is input and which displays either said optical image or said ultrasonic image.

7. An endoscope apparatus according to claim 4, wherein said display means includes a first display apparatus to which said video signal of said optical image is input to display said optical image and a second display apparatus to which said video signal of said ultrasonic image is input to display said ultrasonic image.

8. An endoscope apparatus according to claim 1, wherein said imaging means has a solid-state imaging device.

9. An endoscope apparatus according to claim 8, wherein said solid-state imaging device is provided at said distal end portion of said inserting section of said endoscope.

10. An endoscope apparatus according to claim 8, wherein said optical-image signal processing means includes solid-state imaging device drive means for delivering a drive pulse to said solid-state imaging device and video signal processing means for processing an output signal of said solid-state imaging device, said ultrasonic-image signal processing means includes ultrasonic probe drive means for delivering a drive pulse to said ultrasonic probe and video signal processing means for processing an output signal of said ultrasonic probe.

11. An endoscope apparatus according to claim 10, further comprising controlling means for controlling said solid-state imaging device drive means and said ultrasonic probe drive means in such a manner that, when said still optical image is to be displayed by said memory control means, driving of said solid-state imaging device is stopped, while, when said still ultrasonic image is to be displayed by said memory control means, driving of said ultrasonic probe is stopped.

12. An endoscope apparatus according to claim 10, further comprising control means for stopping the delivery of said drive pulse by said solid-state imaging device drive means during a period of time when said drive pulse is being output from said ultrasonic probe drive means.

13. An endoscope apparatus according to claim 1, wherein said ultrasonic probe is to effect electronic scanning.

14. An endoscope apparatus according to claim 1, wherein said ultrasonic probe is to effect mechanical scanning, and said endoscope further includes a mechanically driving means for allowing said ultrasonic probe to effect mechanical scanning.

15. An endoscope apparatus according to claim 10, wherein said ultrasonic probe is to effect mechanical scanning, and said endoscope further includes a mechanically driving means for allowing said ultrasonic probe to effect mechanical scanning.

16. An endoscope apparatus according to claim 15, further comprising a control means for stopping the driving of said ultrasonic probe by said mechanically driving means during a period of time when said drive pulse is being delivered from said solid-state imaging device driving means to said solid-state imaging device.

17. An endoscope apparatus according to claim 1, further comprising a light source for supplying illumination light to said illumination light means, wherein said optical-image signal processing means, said ultrasonic-image signal processing means, said memory control means, and said light source are accommodated in a housing.

18. A signal processing apparatus for use in an endoscope having imaging means and an ultrasonic probe and connected to said endoscope, and said apparatus comprising:
   optical-image signal processing means for signal processing for said imaging means for obtaining an optical image and for generating a video signal of said optical image, said optical-image signal processing means having an optical image memory means for storing said optical image;
   ultrasonic-image signal processing means for signal processing for said ultrasonic probe for obtaining an ultrasonic image and for generating a video signal of said ultrasonic image, said ultrasonic-image signal processing means having an ultrasonic image means for storing said ultrasonic image; and
   memory control means for controlling writing and reading by said optical imagae memory means and ultrasonic image memory means, for simultaneously outputting a video signal for displaying a moving ultrasonic image and a video signal for displaying a still optical image when a moving ultrasonic image is viewed and for simultaneously outputting a video signal for displaying a moving optical image and a video signal for displaying a still ultrasonic image when a moving optical is viewed.

19. A signal processing apparatus for use in an endoscope according to claim 18, wherein said optical image memory means and said ultrasonic image memory means are respectively constituted by frame memories.

20. A signal processing apparatus for use in an endoscope according to claim 19, wherein said memory control means for displaying said still optical image and said still ultrasonic image by prohibiting writing in said frame memories.

21. A signal processing apparatus for use in an endoscope according to claim 18, further comprising synthesizing means for synthesizing said video signal of said optical image and said video signal of said ultrasonic image.

22. A signal processing apparatus for use in an endoscope according to claim 21, further comprising changeover means for outputting either said video signal of said optical image or said video signal of said ultrasonic image by changing over the same.

23. A signal processing apparatus for use in an endoscope according to claim 18, wherein said optical-image signal processing means is to effect signal processing for said solid-state imaging device serving as said imaging means.

24. A signal processing apparatus for use in an endoscope according to claim 23, wherein said optical-image signal processing means includes a solid-state imaging device drive means for delivering a drive pulse to said solid-state imaging device and a video signal processing means for processing an output signal of said solid-state imaging device, said ultrasonic-image signal processing means includes an ultrasonic probe drive means for delivering a drive pulse to said ultrasonic probe and a video signal processing means for processing an output signal of said ultrasonic probe.

25. A signal processing apparatus for use in an endoscope according to claim 24, further comprising a control means for controlling said solid-state imaging device drive means and said ultrasonic probe drive means in such a manner that, when said still optical image is to be displayed by said memory control means, driving of said solid-state imaging device is stopped, while, when said still ultrasonic image is to be displayed by said memory control means, driving of said ultrasonic probe is stopped.

26. A signal processing means for use in an endoscope according to claim 24, further comprising controlling means for stopping the delivery of said drive pulse by said solid-state imaging device drive means during a period of time when said drive pulse is being output from said ultrasonic probe drive means.

27. A signal processing apparatus for use in an endoscope having imaging means and an ultrasonic probe and connected to said endoscope, said apparatus comprising:
   optical-image signal processing means for signal processing for said imaging means for obtaining an optical image and for generating a video signal of said optical image, said optical image signal processing means having an optical image memory means for storing said optical image;
   ultrasonic-image signal processing means for signal processing for said ultrasonic probe for obtaining an ultrasonic image and for generating a video signal of said ultrasonic image, said ultrasonic-image signal processing means having an ultrasonic image memory means for storing said ultrasonic image; and
   memory control means for controlling writing and reading by said optical image memory means and said ultrasonic image memory means and for displaying a still optical image and a still ultrasonic image.

* * * * *

UNITED STATES PATENT AND TRADEMARK OFFICE
CERTIFICATE OF CORRECTION

PATENT NO.  : 4,869,256
DATED       : September 26, 1989
INVENTOR(S) : KANNO et al It is certified that error appears in the above-identified patent and that said Letters Patent is hereby corrected as shown below:

On the cover page, Item [75], before "all of Japan" add the following inventors:  --Takeaki Nakamura, Hino; Yoshikazu Tojo, Hachioji; Shinichi Nishigaki, Tokyo; Hiromasa Suzuki, Akishima,--.

Signed and Sealed this

First Day of January, 1991

Attest:

HARRY F. MANBECK, JR.

*Attesting Officer*    Commissioner of Patents and Trademarks